United States Patent
Sarofim (10) Patent No.: US 7,919,063 B2
(45) Date of Patent: Apr. 5, 2011

(54) DEVICE WITH A COMPRESSIBLE MATRIX HAVING HOMOGENEOUS FLOW PROFILE

(75) Inventor: Emad Sarofim, Hagendorn (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 196 days.

(21) Appl. No.: 12/064,992

(22) PCT Filed: Sep. 5, 2006

(86) PCT No.: PCT/EP2006/008629
§ 371 (c)(1),
(2), (4) Date: Feb. 27, 2008

(87) PCT Pub. No.: WO2007/028569
PCT Pub. Date: Mar. 15, 2007

(65) Prior Publication Data
US 2008/0206111 A1      Aug. 28, 2008

(30) Foreign Application Priority Data

Sep. 6, 2005   (EP) .................................... 05108133

(51) Int. Cl.
*B01D 11/00*         (2006.01)
(52) U.S. Cl. ....... 422/513; 422/68.1; 422/502; 422/504; 422/51; 210/496; 210/506; 210/435; 210/446; 210/505
(58) Field of Classification Search ............. 422/99, 422/68.1, 100, 101, 102, 61, 58; 210/496, 210/506, 435, 446, 505, 508, 509
See application file for complete search history.

(56) References Cited

U.S. PATENT DOCUMENTS

| | | | |
|---|---|---|---|
| 4,052,779 A | 10/1977 | Hunter | |
| 5,556,789 A | 9/1996 | Goerlach-Graw et al. | |
| 5,910,246 A | 6/1999 | Walter et al. | |
| 6,090,936 A | 7/2000 | Walter et al. | |
| 6,190,569 B1 * | 2/2001 | Parker | 210/770 |
| 6,391,265 B1 * | 5/2002 | Buechler et al. | 422/101 |
| 6,537,501 B1 | 3/2003 | Holl et al. | |
| 7,192,559 B2 * | 3/2007 | Chow et al. | 422/100 |
| 2002/0114990 A1 | 8/2002 | Fly et al. | |

FOREIGN PATENT DOCUMENTS

| | | |
|---|---|---|
| EP | 0200362 A2 | 12/1986 |
| EP | 0236069 A2 | 9/1987 |
| EP | 0236069 A3 | 9/1987 |
| EP | 0200362 B1 | 1/1993 |
| EP | 0738733 A2 | 10/1996 |

(Continued)

*Primary Examiner* — In Suk Bullock
*Assistant Examiner* — Sharon Pregler
(74) *Attorney, Agent, or Firm* — Charles M. Doyle; Olga Kay; M. Reza Savari (57) ABSTRACT

A fluidic device containing a flow through chamber comprising an inlet port, an outlet port, and a fluid permeable, compressible matrix located in the chamber between said inlet port and said outlet port, and said compressible matrix having a higher flow resistance at higher compressions and a plurality of flow paths leading from said inlet port to said outlet port through said matrix comprising shorter and longer length flow paths, wherein said matrix is compressed in at least one dimension, being more strongly compressed along the shorter length flow paths than along the longer length flow path.

20 Claims, 7 Drawing Sheets

FOREIGN PATENT DOCUMENTS

| | | |
|---|---|---|
| EP | 0738733 A3 | 1/1997 |
| EP | 0236069 B1 | 5/1997 |
| EP | 0543942 B1 | 1/2001 |
| EP | 0738733 B1 | 10/2001 |
| EP | 2006008629 | 9/2006 |
| EP | 0543942 B2 | 11/2006 |
| JP | 2004163161 * | 6/2004 |
| JP | 2004163161 A | 6/2004 |
| WO | 9202638 | 2/1992 |

* cited by examiner

DEVICE WITH A COMPRESSIBLE MATRIX HAVING HOMOGENEOUS FLOW PROFILE

FIELD OF THE INVENTION

The present invention relates to fluidic devices having a flow-through cell containing an inserted matrix, a method and an instrument for manufacturing a fluidic device, a system including said device and methods of use for such device.

The field of application of the fluidic device according to the invention is various, depending upon the matrix, e.g. a solid phase adsorber, filter, solid phase-reactor. The device has improved fluidic behavior and is easy to produce.

BACKGROUND OF THE INVENTION

Devices useful for conducting chemical reactions have found widespread applications. Particularly, in chemical analyses, e.g. for the determination of constituents of body fluids like cholesterol in blood, devices containing fleece for the removal of constituents disturbing further analysis, e.g. cells, are commonly used. Furthermore, from EP 0 738 733 devices for separating nucleic acids from body fluids are known. However, this device is does not integrate sample preparation and detection. Integrated devices have the advantage of safety, protection from contamination and possibility of combination with other functions, e.g. detection.

More complex analyses need more sophisticated devices. For example, in U.S. Pat. No. 6,537,501 a cartridge is disclosed comprising micro fluidic flow channels and more extended compartments, like a waste collection container.

In JP 2004-163161 a device having a generally flat compartment with parallel upper and lower side walls containing a matrix for separating nucleic acids is disclosed. Therein, several layers of a fleece are inserted into the compartment and get uniformly compressed to increase extractability of nucleic acids. Therefore, the fluid flow is inhomogeneous. This has the consequence of lower binding capacity of the fleece and a need of higher fluid volume.

It was an object of the present invention to provide a device for improved robustness in use.

SUMMARY OF THE INVENTION

A first subject of the invention is a fluidic device containing a flow through chamber, said chamber comprising
  an inlet port,
  an outlet port, and
  a fluid permeable, compressible matrix located in the chamber between said inlet port and said outlet port, said compressible matrix having a higher flow resistance at a lower value of the Degree of Compression compared to at a higher value of the Degree of Compression, and a plurality of flow paths leading from said inlet port to said outlet port through said matrix comprising shorter length flow paths and longer length flow paths,
wherein said matrix is unequally compressed in at least one dimension, being stronger compressed in the shorter length flow paths than in the longer length flow path.

Still another subject of the invention is a fluidic device containing a flow through chamber, said chamber comprising
  an inlet port,
  an outlet port,
  side walls,
  an upper wall and a lower wall, the maximum distance between said upper wall and said lower wall being no more than 20 mm, more preferably between 5 and 0.3 mm, most preferably between 0.3 and 3 mm, and
  a fluid permeable, compressible matrix located between said inlet port and said outlet port, said compressible matrix having a higher flow resistance at higher compression rate, a plurality of flow paths leading from said inlet port to said outlet port through said matrix comprising shorter and longer flow paths,
wherein along the various flow paths the average distance between said upper wall and said lower wall is smaller for said shorter length flow paths than for said longer length flow paths.

Furthermore, a subject of the invention is a method for the manufacturing of a fluidic device containing a flow through chamber having an inlet port and an outlet port, said chamber containing a piece of compressible matrix, said compressible matrix having a higher flow resistance at stronger compression compared to at a weaker compression, comprising the steps
  a preparing a piece of said compressible matrix having a size which is larger than the size of said chamber,
  b inserting said piece into said chamber through an opening in said device, and
  c covering said opening by a sealing wall and thereby unequally compressing the matrix.

DETAILED DESCRIPTION OF THE INVENTION

The present invention has found that in order to
equally distribute compounds over the matrix, particularly to evenly adsorb or immobilize a substance present in a fluid flowing through the matrix
or
  wash the matrix (washing=removal of fluid remaining in the open space within the matrix or removal of matter adsorbed or bound to the surface of the matrix)
or
  perform a reaction between the fluid or matter carried in the fluid and the surface of the matrix.
or
  desorb or dissolve matter from the surface of a matrix
or
  separate a matter by size-exclusion (or filtering), it is preferred to reduce flow on shorter length flow paths compared to longer length flow paths. Preferably, the time of a volume element remaining in the matrix should be essentially the same for each flow path. In other words, the front of different volume elements flowing on different flow paths reach the outlet port at about the same time. Preferably, the flow-through time (Time used by a finite volume element to pass the matrix) does not vary significantly for the longer and the shorter (geometrically understood) flow-paths. Preferably the flow-through-time varies less than +/−20% for all flow-paths (relative to the average flow-through-time), more preferably less than +/−10%, most preferably 0%.

A first embodiment of the invention is a fluidic device containing a flow through chamber, said chamber comprising
   an inlet port,
   an outlet port, and
   a fluid permeable, compressible matrix located in the chamber between said inlet port and said outlet port, said compressible matrix having a higher flow resistance at stronger compression rate compared to at weaker compression rate, and a plurality of flow paths leading from said inlet port to said outlet port through said matrix comprising shorter length flow paths and longer length flow paths,
wherein said matrix is unequally compressed in at least one dimension, being stronger compressed in the shorter length flow paths than in the longer length flow path.

A fluidic device of the present invention is a device useful in receiving a fluid or/and storing a fluid or/and chemically or physically treating a fluid, or/and analyzing a fluid. The fluidic device is preferably a consumable or disposable device. A disposable device is a device that is usually discarded after single use. The fluidic device may additionally contain other elements, such as channels and chambers having particular functions, e.g. for holding and processing a fluid, electrodes for measuring a physical property, a sensor, a chamber or channel suitable to perform a measurement, a reagent-container or detection cell, or interfaces to instruments or human interfaces operating the fluidic device.

The size of the fluidic device according to the invention is mainly determined by the amount of fluid to be treated, held or processed. If the fluidic device contains other elements, the size is also determined by the space-requirements of the other functions implemented in the fluidic device.

In a preferred embodiment the matrix is used to isolate and purify nucleic acid from a sample of biological origin e.g. blood-plasma, e.g. for nucleic-acid-testing (e.g. genetic testing), the total volume of the sample processed over the matrix is 50 µl and the outer volume of the fluidic device harboring the matrix is 5 ml.

The total fluid-volume processed over the matrix is in a range of 10 µl and 1000 ml. The volume of the device is in a range of between 0.5 an 1000 ml, more preferably for in vitro diagnostic application in a range of between 0.5 and 50 ml.

Preferably, the fluidic device has a substantially flat structure, i.e. in its main part it has a thickness of less than 50 mm, preferably of between 0.2 and 15 mm, a length and width of less than 300 mm, preferably of between 10 and 150 mm. If parts of the device need larger thickness, this part may exceed over the substantially flat structure.

In case of supplemental elements, such as inlets, reagent containers, detection cells, mechanical and thermal interfaces, etc. e.g. for receiving and maintaining a fluid, the device may have a body which further contains one or more cavities, which temporarily or continuously receive or/and maintain a fluid or a fluid derived therefrom. Cavities formed within the body preferably have dimensions, which are suitable for the intended use of the process to be performed in the device. Typical volumes of such cavities can range from 1 µl to 1 L, preferably from 5 µl to 100 ml, more preferably from 10 µl to 10 ml. This cavity can have different forms adapted to the various intended uses of the device. The cavity preferably comprises multiple sections such as channels or/and chambers. A preferred fluidic device contains one or more chambers and two or more channels.

A channel of the device according to the invention is an extended cavity having a length which is larger than its breadth and height. The length of a channel is defined to be the dimension in which the main flow of fluid through the channel is effected. The breadth and the width make up the cross section of the channel. Channels formed in the device, preferably the body, preferably have a cross section of less than 10 $mm^2$, preferably of between 0.01 and 2 $mm^2$.

The flow through chamber present in the fluidic device harboring the matrix of the present invention has a volume of between 1 µl and 10 ml. Preferably, a chamber for separating nucleic acids from a fluid will preferably have a volume of between 5 and 100 µl. The chamber preferably is flat. Flat in the present invention means that the maximum extension of the chamber in a first dimension is at least 2 times, more preferably 5 times, and most preferably 10 times larger than the minimum extension of said chamber in a second dimension perpendicular to the first dimension. Preferably, the extension in a third dimension perpendicular to said second dimension and said first dimension is between the extensions of said first and second dimensions, more preferably is between 0.2 times and 5 times the extension in the first dimension. Based on this the first dimension is the breadth, the second dimension is the height and the third dimension is the length of the chamber.

Realization of such flat chamber leads to a chamber having generally two large substantially opposing walls, in the following called upper and lower wall, irrespective of whether those walls are arranged vertically or horizontally in the final working position of the device.

The breadth of the chamber is limited by what in the following is called side walls. The breadth of the chamber may vary in a broad range over the length of the chamber. Preferably, the breadth of the chamber is smallest in the beginning and the end of the chamber, and is largest in the middle of the chamber. The side walls may be straight or curved. Preferably, the side walls are curved to not comprise any sharp edges or recesses, as those may increase the risk of retaining gaseous components during use of the device which could yield in inefficient performance, e.g. inefficient nucleic acid purification. The distance between the upper wall and the lower wall will thus be considered to be the height of the chamber.

Preferably, the ratio of the maximum distance between the side walls of the chamber and the maximum distance between the upper wall and the lower wall of the chamber is between 2:1 and 500:1, more preferably between 4:1 and 40:1, and most preferably between 5:1 and 15:1.

Preferably, the ratio of the length of the matrix (measured along said shortest flow path) to the breadth of said matrix is between 20:1 and 1:20, more preferably between 5:1 and 1:5 and most preferably between 2:1 and 1:2.

Preferably, the geometry of said chamber is symmetric relatively to a plane perpendicular to the breath.

Preferably, the shape of the matrix is circular or rectangular with rounded corners or any other geometry which is easily shapeable e.g. by punching or other cutting tool in two dimensions and flat in the height. More preferably, the shape of the matrix for the circular chamber is a cylinder. Preferably, the chamber harboring the matrix must have a shape to receive the matrix such that the result of the assembly of the matrix in the chamber is without fluidic shortcuts between the inlet port and the outlet port.

The chamber may fully or partially filled by the matrix. Sections not filled by matrix are found in the areas of the inlet and outlet port.

The smallest dimension of the chamber will preferably be the height, which will be between 100 µm and 50 mm, preferably between 200 µm an 20 mm, more preferably between 300 µm and 2500 µm, while the length and breadth of the chamber may be between 500 µm and 50 mm, preferably between 2 mm and 20 mm. Very preferred, the chambers are flat chambers of a height of less than 3 mm, preferably between 500 µm and 2 mm. Preferably, the minimum distance between the upper wall and the lower wall is between 0.2 and 3 mm.

The flow through chamber according to the invention comprises at least one inlet port and at least one outlet port. Those ports are designed to allow fluid to be treated in said chamber to flow through, i.e. enter, pass through and exit the chamber. For efficient use of the matrix in the chamber, the ports are preferably located at opposing positions of the chamber, more preferably on positions to allow the fluid to enter the chamber in a flow direction parallel to the upper and lower walls. The distance between the inlet and the outlet port thus is preferably the length of the chamber.

The channels are leading to the chamber and leading out of the chamber, respectively.

A chamber can have more than one inlet or/and more than one outlet ports. In case of more than one ports, those ports are preferably arranged symmetrically regarding the chamber.

The shape of the inlet and outlet ports can be chosen to provide a smooth transition from the channel(s) into and from the chamber. Preferably, the channel widens when reaching the chamber, thus forming an inlet or outlet port with a diameter larger than the general diameter of the channel. Widening of the channel improves smooth entering of the fluid into the chamber.

Figure 1:
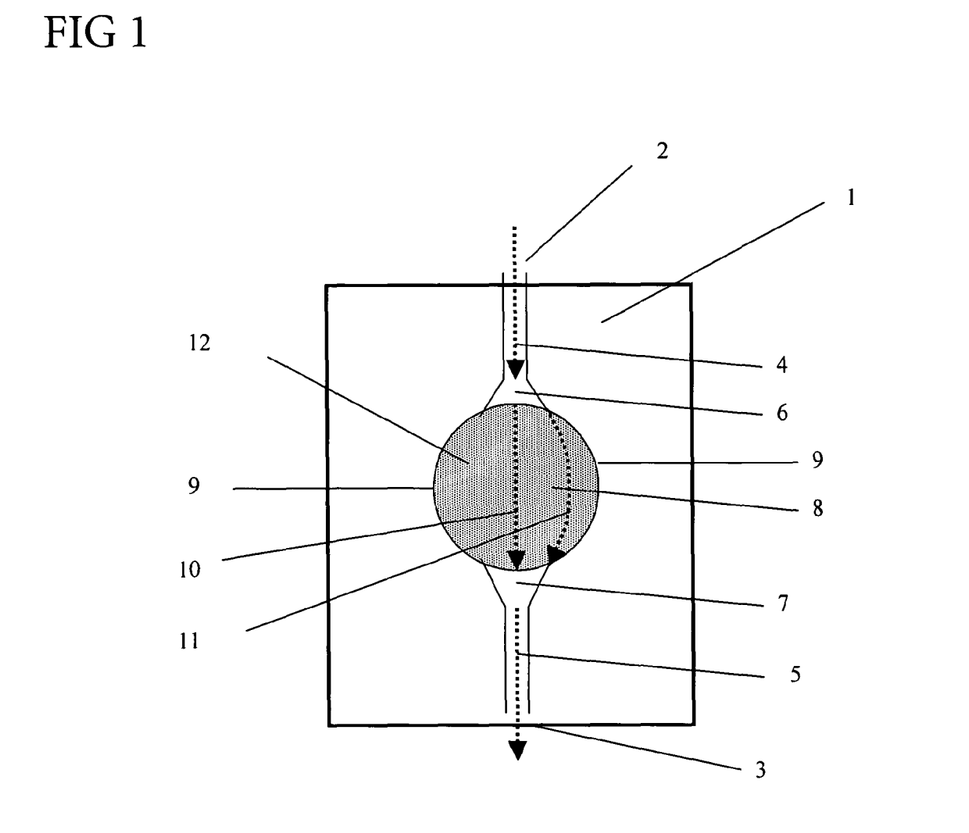
In FIG. 1 there is shown schematically a device having a circular chamber through which a fluid can be passed from an inlet port to an outlet port and the possible flow paths therein.

A first device according to the invention, wherein the chamber is generally flat, is shown in FIG. 1. The device (1) contains a fluid introduction port (2) and a fluid removal ports (3) located on sides of the device (1). Two channels (4) and (5) are leading from the exterior of the device through inlet port (6) and outlet port (7) into the chamber (8) in the body. Thus, the fluid port can be pierced from the flat side of the device.

As can be understood from the above, a fluid introduced into the chamber through the inlet port will have a plurality of theoretical possibilities to flow through matrix in the chamber to arrive at the outlet port and leave the chamber. The theoretical ways leading through the chamber from the inlet to the outlet are in the following called flow paths. Those flow paths are flow paths for a fluid. The shortest flow path will generally be as long as the length of the chamber. Some of those flow paths are longer, depending upon their distance from the shortest flow path. The farther the flow path is apart from the shortest flow path, the larger it will be. For example, a flow path along a side wall will be very long and may even be the longest flow path through a chamber.

The arrangement of flow paths through the chamber is schematically shown in FIG. 1. The figure shows a cut through the chamber in parallel to the upper and lower walls. There is shown a side wall (9), a longer length flow path (10) and a shorter length flow path (11).

Conveniently, the body of the device is formed from at least one relatively rigid polymer. Polymers for the body according to the present invention are preferably selected from the group of thermoplastic material, for example, polypropylene, polyethylene, polystyrene, polycarbonate and polymethylmethacrylate. Further preferably, the body is made of a material, which can be liquefied by heating above its melting temperature, and which in molten state can be introduced into a mold to reflect the particular form the body or a part thereof is intended to assume.

In the chamber there is located a piece of matrix. The material for the matrix depends upon the particular intended use of the matrix. For example, for purifications of components from a fluid on a solid phase, the matrix will be chosen from a material capable of binding the component, preferably also capable of releasing the component from the solid phase under changed conditions. Suitable matrices according to the invention are porous materials, i.e. are fluidically permeable. Preferred matrices are selected from the group of fleece made of fibers. e.g. a preferred matrix for the isolation and purification of DNA is glass fiber fleece. Depending on the field of application the material of the matrix is selected from sintered porous plastic, cellulose fibers, glass-fibers or polymer fibers. The material may have the property to selective absorb/desorb classes of matter, such as an ion exchanger, be a carrier of reagents, or be a sieving matrix.

The matrix is located between inlet port and outlet port in order to force the fluid entering the chamber at the inlet port and passing the chamber to said outlet port to flow through the matrix. The matrix will be located within the chamber to at least once fully cover the cross section of the chamber. The full covering of at least one cross-section located between the inlet and outlet of the chamber guarantees that there is no substantial flow through the chamber without passing at least a part of the matrix. Substantial in this context is a flow of fluid of more than 95% flowing through the matrix. The compression of the matrix in the chamber depends upon the properties of the matrix (preferred are matrices which are highly compressible, e.g. certain glass fiber fleeces, are compressible to a volume down to 35% of the uncompressed volume).

An essential feature of the invention is that the matrix is fluid permeable and compressible. This matrix has an Outer Volume (also called here "shell volume") which is defined by the outer shape of the piece of matrix. Permeable means that a fluid can flow through the matrix, by applying a differential pressure or gravity.

A matrix is compressible in the sense of the present invention, if its Outer Volume is reduced by applying pressure to the matrix, i.e. by pressing a surface against a surface of the matrix. By such action, the Outer Volume of the matrix will be reduced to a certain extend. The Degree of Compression DC (in %) of the matrix is defined according to the present invention to be the Outer Volume in compressed status divided by the Outer Volume in uncompressed status multiplied by 100.

The Outer Volume of the piece of matrix can be determined in uncompressed status by known means, for instance by metering the outer dimensions of the piece of matrix. The Outer Volume of the piece of matrix in compressed status can be metered the same way, but when compressed. The Inner Volume of the piece of matrix can be determined by known means, for instance by metering the amount of a fluid that can in maximum enter into the piece of matrix.

As the piece of matrix will preferably resemble the interior shape of the chamber, the preferred shape of the matrix is flat in uncompressed status. In dimensions where a compression is desired in the final assembly, the matrix will preferably have a larger shape before being compressed during assembly.

For this invention, the matrix is considered to be homogenous and the flow paths will be the macroscopic flow paths, without considering micro-structural disturbances. In real life a fluid-element will pass through the matrix in a much more complicated way, than here discussed. Regarding the microscopic structure of the fleece for a fluid element one could observe a much complexer movement e.g. flowing through pores of various diameter, or flowing around single fiber fleeces. Fluid will deviate in reality from the theoretical path using a homogenous flow resistance, to circumvent any fiber on the theoretical path and may return to the theoretical path after having passed the fiber.

A core of the invention is that the matrix within the chamber is compressed unequally on different flow paths through the chamber. This means that the Degree of Compression (in the following also abbreviated as DC) differs at different locations in said chamber. The Span of Degree of Compression (in the following also abbreviated as SDC) at locations compared is defined to be the Highest value of the Degree of Compression (in the following also abbreviated as HDC) minus the Lowest value of the Degree of Compression (in the following also abbreviated as LDC) at the locations compared. The HDC could be the DC of the matrix in uncompressed status, and the LDC could be between the HDC and the fully compressed matrix, i.e. the matrix virtually without any significant Inner Volume. As used herein, stronger compression means a lower DC value and weaker compression means a higher DC value.

Typical DC values according to the present invention are equal or less than 100% (uncompressed), preferably between 100 and 10%, more preferably between 95 and 20% and most preferably between 90 and 25%. Typical Spans of Degree of Compression (SDC) of the present invention are more than 5%, preferably between 5 and 70% and most preferably between 5 and 50%.

At equal compression of a matrix with unequal lengths of flow-paths, unequal flow-through-times of the volume elements following the flow-paths are observed. By appropriate unequal compression of the matrix, the flow through times of volume elements following the various flow-paths can get at least partially equalized. Ideally all flow paths have the same flow through time after equalization. Generally already partial equalization of the flow through time by adaptive modulation of the flow resistance by compression of the matrix gives advantages as described above.

The local distribution of the DC on the various paths can differ in many ways.

The averaged DC along a flow path is defined as the term Average Degree of Compression (also called ADC in the following).

Generally to achieve an at least partial equalization of the flow-through-times of the longer and shorter flow paths, the ADC-values of the longer length flow paths are held larger (weaker compressed) than the ADC-values for the shorter length flow path Equal flow-through times with an equal matrix compression are otherwise only achievable for a design where there are equal length flow passes implemented. As example one can imagine a cubic shape matrix having the inlet and outlet on two opposite walls. Such devices can be imagined, but may have several disadvantages. A major disadvantage is its reliable production, mainly to fulfill reliable the aspect of having no significant fluidic shortcuts. Therefore designs having not equal length flow paths may offer a supplemental degree of freedom for designs, mainly taking into respect the reliable production and to avoid such difficulties in the production (e.g. by using rounded shaped matrices).

According to the invention, the DC of the matrix varies on at least one section of the device. Then the DC at such a location on said flow path may differ from the ADC, i.e. will be smaller or bigger than the DC and at another location. The DC can vary from 100% (uncompressed) and may go to its maximal compression (which is defined by matrix property and the applicable compression force, e.g. for a glass fleece down to DC=30%). However, the DC will not be so low that flow is totally inhibited. Preferably a flow path with a lower ADC (averaged over the flow path) will be a flow path of shorter length. Therefore, it is not excluded from the invention that a shorter length flow path has on its path a location of LDC compared to a longer length flow path. In this case, however, the ADC of the shorter flow path will be lower than the ADC of the longer flow path. Furthermore, a man skilled in the art may take the risk of using a small amount of longer length flow paths that do not have the superior characteristics of having the Lower DC as envisaged according to the invention, if the treatment result is not substantially affected. Such embodiments should not escape the scope of the invention.

Figure 2:
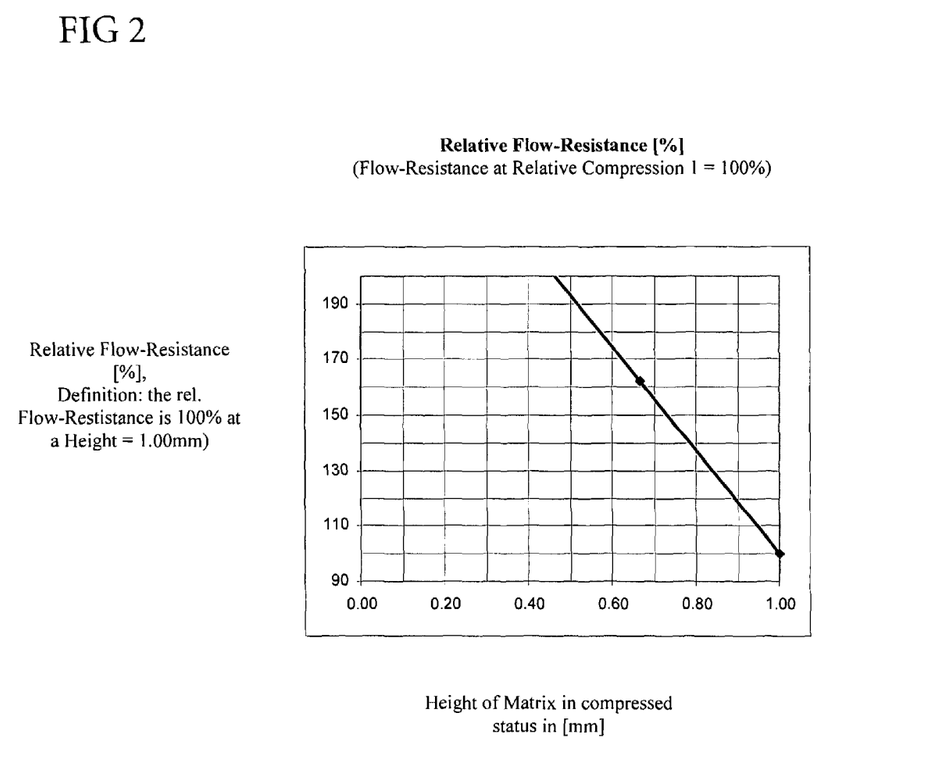
In FIG. 2 there is shown a diagram giving the relationship of the Degree of Compression and the flow resistance.

To achieve a more homogeneous flow, in a second embodiment of the invention, the matrix as used in the present invention has a higher flow resistance at stronger compression, i.e. at lower DC. This means that the flow resistance is increased when the matrix is compressed. This is also evident from FIG. 2, where the flow resistance is shown (expressed as reciprocal flow-rate at a constant pressure) for different degrees of compression (the smaller the height of the matrix in compressed state, the lower the degree of compression (DC) after compression and the higher the flow resistance.

Therefore, in a first embodiment of the invention, the matrix is unequally compressed in at least one section of the matrix in at least one dimension, being in an average stronger compressed along the shorter length flow path than along the longer length flow path.

Following the above principals, the height of the chamber, the compression profile and the height of the matrix in non-compressed state can be modified to design a device having a flow characteristic according to the needs of the particular use or assay. Defined DCs at a particular location in a chamber can be achieved by several means. In general higher compressions are applied to sections where there are to high flow rates. An easy way to achieve an optimized design (flow) is by iterative design steps. Successively compressing the areas where there is a to high flow rate observed. Sections of too high flow rate, can get corrected to lower flow rates by reducing the height of the chamber at these sections causing a lower DC-value and therefore rising the flow resistance in these sections. By successively decompressing areas where there is a too low flow rate observed by enlarging the height in these areas the flow resistance is reduced and therefore the flow through time through theses areas is reduced.

In the context of this invention, flow resistance is the resistance that is imposed by the matrix upon a volume element of a fluid when passing the matrix on a flow path.

Another embodiment of the invention is a flow through device containing a flow through chamber, said chamber comprising an inlet port, an outlet port, side walls, an upper wall and a lower wall, the maximum distance between said upper wall and said lower wall being no more than 20 mm, a fluid permeable, compressible matrix located between said inlet port and said outlet port, and a plurality of flow paths leading from said inlet port to said outlet port through said matrix comprising shorter and longer flow paths, wherein the average distance along the various flow paths between said upper wall and said lower wall is smaller for said shorter flow paths than for said longer length flow paths.

The maximum distance between the upper wall and the lower wall of the chamber is more preferably between 0.3 and 5 mm, most preferably between 0.3 and 3 mm. This embodiment of the invention is directed to the measure to reduce the height of the chamber at locations on the shorter length flow paths compared to locations on the longer length flow path, thereby compressing the matrix to enhance the flow resistance in said flow path.

Preferably, the height of the chamber or distance between the upper wall and the lower wall varies within 100% and 20% of the largest height of said chamber. This means that the height of the chamber is reduced by up to 80% of the maximum height in the chamber. The average height measured along at shorter length flow paths will generally be smaller than the average height measured along longer length flow paths.

In the more general sense of the invention, preferably, the matrix is unequally compressed in said chamber in at least one dimension orthogonal to the flow direction.

While in a simple mode of the invention, the fluidic device may contain just the parts as outlined above, the final device preferably is a composite of several elements. This means it consist of two or more parts manufactured separately and assembled subsequently, one part of the device being a body comprising a cavity, more preferably the chamber as outlined above. Chamber(s) or/and channels may be contained in separate parts. Because it has proven to be difficult to manufacture a body comprising a cavity suitable for chemical analyses in one piece, it is preferred that the device is made of two or more parts, which are combined to create the one or more cavities.

In a very preferred embodiment, the device comprises a first element called "body" having channels and/or grooves having one side open to the environment. Preferably, the body is rigid and provides the stiffness or rigidity to the device to maintain the shape of the cavity throughout the process of manufacture and use of the device. A second element called "sealing wall" is an element used to close the open side of said grooves or/and channels. The sealing wall can be of any material but in general has to tightly close the fluidic system around the chamber containing the matrix. Suitable materials are known to those skilled in the art.

During assembly of the fluidic device, pressure is applied to force the matrix into the chamber. This is easily done by pressing the sealing wall on its full surface to the surface surrounding the groove of the body. By attaching, mounting or sealing the second element to the first element, the form of the cavity of the final device is fixed. Furthermore, the matrix is fixed and compressed within the chamber.

Preferably supplementally the matrix is also compressed in a second dimension, e.g in its length and/or breath. This supplemental compression has the advantage that the risk of flow fluidic shortcut relevant for the result of the treatment in the chamber besides the matrix is reduced, forcing the majority of the liquid to pass the matrix and do not go via a by-pass. A preferred mode of manufacture to this effect will be disclosed below.

Thermo sealable foils are generally composites of several materials, wherein the layer opposed to the sealing is able to seal to the body. A typical foil suitable to be joined to a polypropylene body has composite layers of aluminum or polyester and polypropylene. Such sealing foils are known and are commercial available. In the case where, the sealing wall is a foil, the foil preferably is between 20 and 1000 μm thick, more preferably between 50 and 250 μm.

Heat transferring walls, like aluminum foils, or heating elements may be integrated into either the sealing wall or the body. The heat transferring wall can be used to heat or/and cool fluids contained in the device.

As will be evident from the above, the form of the groove will determine the shape of the chamber in the final device in the various dimensions of the chamber. For example, the depth of the groove compared to the surrounding area of the body can be used perfectly to define the height of the chamber in case a flat sealing wall is used to close the groove. The width of the groove can perfectly resemble the breadth of the chamber and the length of the groove resembles the length of the chamber. In order to compress the matrix, the depth of the groove is smaller than the height of the matrix in uncompressed status. The depth at the particular locations of the groove is the larger the higher the DC is intended to be at the respective locations of the chamber. Obviously, if the final height of the chamber is reduced by a part of the device which is not the body, e.g. the sealing wall closing the opening, any protrusion of said part may be used to compress the matrix. Then, the height of the chamber will be defined one or the other or by both parts defining the chamber (or even more).

The device can contain further elements that may be useful for the intended purpose of the device.

In order to introduce fluid into or/and remove fluid from the cavity in the body, the device according to the present invention may have one or more fluid ports allowing introduction or removal of fluid into and from the cavity of the device.

In another embodiment, electrodes can be incorporated into the body or the sealing wall. Electrodes can be used to determine the electrochemical status of fluids contained in the device or to start electrochemical reactions within the device. In this case, the device will have appropriate connectivity to electrical circuits.

The device may have additional fluidic or micro fluidic functions. Those functions are generally known to be functions for physically treating the fluid in a cavity. Those can be static elements, like fittings, comprising walls and surfaces, for example for mixing, dividing or combining of fluids.

Other functions that may be provided by the cavity are optical functions. For this reason, the body around said cavity, preferably a chamber, incorporates an optical window (allowing an at least partial transmission to a wavelength), e.g. is transparent to allow entering or/and escaping light from the cavity to the outside of the device. Preferably, the cavity has dimensions that allow collecting fluid in an amount that is sufficient for reliable detection of components contained in the fluid. Another function of the cavity may be to receive materials to react with the fluid. Such materials may be selected from the group of soluble or insoluble reagents, or combinations thereof, or both, even in separate parts of the cavity, or chambers. Soluble reagents may be reagents to support lysis of a sample, to amplify a nucleic acid contained in the sample or a liquid derived therefrom, or to provide a signal when reacting with the components of the sample to be determined. Insoluble reagents may be solids that are designed to immobilize components of the fluid or compounds derived therefrom. Soluble reagents may be deposited on the surface of such solids and are partially or fully dissolved, more or less fast, in the fluid passing through. Appropriate materials are known to the person skilled in the art of nucleic acid sample preparation.

A fluid can be a sample, a reagent, a diluent or a process fluid or a combination thereof or a fluid derived therefrom. Preferably, the fluid is a liquid. More preferably, the liquid is an aqueous solution.

Typical samples are liquids be selected from the group of environmental liquids, like water from a river or a liquid extracted from soil, food liquids, like a juice or an extract from a plant or fruit, or a liquid received from animal or human body, like blood, urine, cerebrospinal liquid, mucus or lymphatic liquid, or liquid derived therefrom, like serum or plasma, or liquids containing components isolated from the before mentioned liquid, like liquids containing purified antibodies or nucleic acids. Typical reagents are solutions of chemical compounds in a solvent, like reagents intended to be used for analysis of other fluids that need to be free of nucleic acids to not interfere with the analysis of the sample.

The invention is particularly useful in methods for the separation of nucleic acids from a sample. Nucleic acid separation is commonly applied in methods for the determination of nucleic acids. Such methods often use enzymatic processes for modifying or/and amplifying nucleic acids. Enzyme activity is frequently affected by constituents of the sample other than nucleic acids, e.g. such ingredients that act as inhibitors of enzymatic activity. Prior to conducting polymerase chain reaction (PCR, EP 0 200 362), polymerase inhibitors are usually removed from the nucleic acids.

In a diagnostic device, the liquid may contain components to be determined in an analysis. Such liquid further can contain additional components useful for the analysis of components of the liquid or reagents for chemical reactions to be performed within the device. Those reagents can comprise labeled binding partners, for instance labeled oligonucleotide probes or dyes.

A further subject of the present invention is a method for the manufacturing of a diagnostic flow through device containing a flow through chamber having an inlet port and an outlet port, said chamber containing a piece of a compressible matrix, comprising the steps a preparing a piece of said compressible matrix having a size which is larger than the size of said chamber and
b inserting said piece into said chamber through an opening in said device, and
c covering said opening by a sealing wall and thereby compressing the matrix.

The device according to the invention can be manufactured in several alternative modes. In the first mode, particularly useful in the first embodiment of the device as outlined above where the height of the matrix is different at different locations, a piece of said compressible matrix having a size which is larger in height than the size of said chamber is prepared, said piece is inserted into said chamber through an opening in said chamber, and said opening is covered by a sealing wall, thereby fixing and compressing the matrix in the chamber.

An opening in the chamber is understood to be an open side of the chamber through which the matrix can be introduced into the chamber. This may adopt a full side of the chamber, so that the part of the device into which the matrix is introduced has the form of a groove. It is well within the spirit of the invention to intermediately compress the matrix more than in the final status, to fit through an opening of the chamber smaller than the matrix.

The piece of matrix can be prepared according to methods known in the art. However, the invention has found that it is very convenient to produce such matrix in reliable quality and quantity by punching the piece out of a large, flat homogenous piece, like a fleece or a bar. The puncher is designed such that it can also be used to transfer the punched piece of matrix from the place of production to the device and place the piece in compressed status into the chamber of the device without manual intervention. For this purpose, the piece of matrix punched from the larger piece will be larger than the extension in the respective dimension of the chamber. Preferably, the piece is up to 100%, more preferably between 5 and 50%, most preferably 10 to 40% larger than the chamber in the dimension it needs to fit into. In the height dimension, the extension of the matrix can be easily defined by the thickness/height of the larger piece. This production method is quite useful for mass production of such devices.

The two parts—body and sealing wall—can be joined by known methods. In the preferred embodiment, wherein the sealing wall is a thin layer and the rigid body is made of polymer, e.g. polystyrene, the two parts can be combined and then sealed by welding, for example LASER welding, ultrasound welding, thermo sealing or gluing.

The joining method, the material of body and the material of the sealing wall have to be selected to fit together. For example, if the joining method is LASER welding, then the bulk material of the body and the sealing wall are of the same material (e.g. polypropylene) but one of the two materials is stained to have absorption for the laser energy. If the joining method is ultrasound welding both materials are typically the same. If the joining method is thermo sealing the sealing wall is a thermo sealable foil adapted to thermically seal to the body.

An exemplary method is described in the following referring to FIG. 7. In a first step (punching of matrix), a puncher tool (16) having a circular knife edge as large as the perimeter of the piece of matrix to be manufactured is pressed against a fleece of the material (12). By pressing and cutting off a piece of matrix, the piece of matrix (21) will enter the central cavity of the puncher and remain therein.

The matrix will be transferred by a tool to the place of assembly of the device. The tool can be the same tool as used for the first step, e.g. the punching tool, or can be different.

In a second step (transfer of punched matrix to cavity), a funnel (19), having a sloped shape from the perimeter of the knife edge to the perimeter of the groove (20), will be added to the end of the puncher tool extending to the groove (20) to give a guide from the puncher to the body (15) of the device. A plunger (18) can be used to move the piece of matrix through the funnel into the groove, thereby compressing the matrix to fit in breadth and length into the groove.

In a third step (closing the device), the puncher tool (18) will be removed from the body, the matrix (21) remaining in the groove. Then the plunger can be removed from the matrix.

Finally, a heat sealable foil (14) is sealed onto the upper surface of the body (15), thereby closing the opening and compressing the matrix to assume the height of the chamber.

Figure 7:
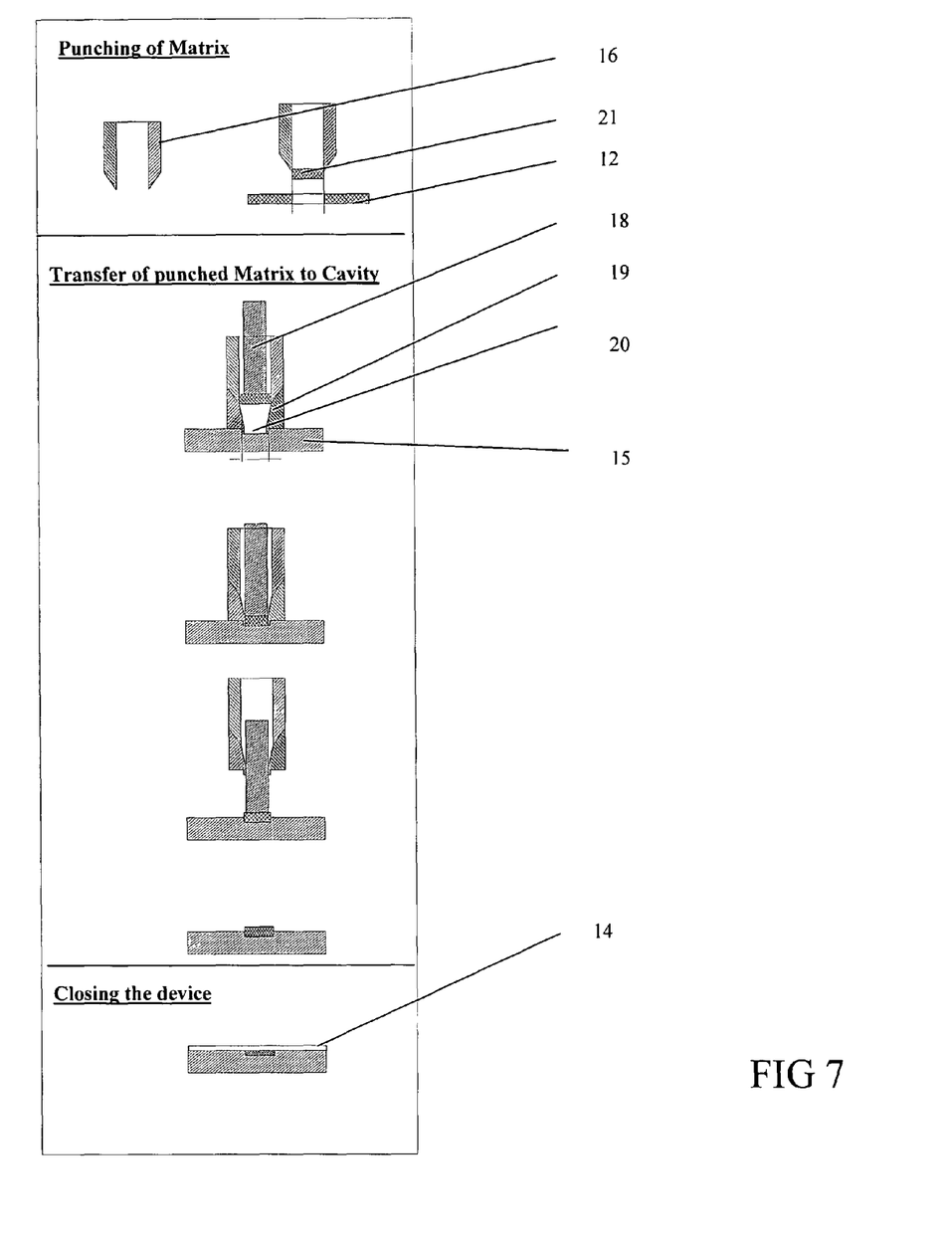
In FIG. 7 there is shown a series of steps for manufacturing a device according to the invention.

While these steps and FIG. 7 show the manufacturing process for a device that does not explicitly show a protrusion in the groove, it is clear from the above description that the process will work the same way with a groove having a protrusion, such that the matrix gets more compressed at the location of the protrusion.

This method is particularly useful for the manufacture of devices comprising a flat chamber where the opening through which the matrix is to be introduced is located on a flat side of said chamber, e.g. where the upper wall is open.

Another subject of the invention is therefore an instrument for manufacturing a flow through device containing a piece of a compressible matrix in a flow through chamber comprising A tool to punch the piece of compressible matrix from an extended piece of compressible matrix to obtain said piece of matrix,
A tool to transfer the punched piece of matrix from the punching tool into the chamber through an opening in said device,
A tool to position a diagnostics flow through device having a chamber to receive a piece of compressible matrix such that it is accessible to said transfer tool, and A tool to guide said piece of compressible matrix into said chamber while said piece gets compressed.

This instrument can not only be used for the manufacturing of the device according to the invention, but to all devices having a lateral compression. Preferably, it can be used in addition to create a horizontal compression in the chamber. The instrument preferably comprises a tool to seal the opening of the chamber, preferably while compressing the matrix horizontally.

Another subject of the present invention is a system for analysis of a fluid comprising an instrument having a fluid delivery module, and
a device according to the invention.

Instruments for analysis of a fluid are generally known. Those include the modules generally required for analyses. Preferred modules for such instruments are optics for determining optical properties or changes in optical properties of the liquid, mechanics to move the liquid from a first position to one or more other positions, and liquid handling modules for dispensing or/and aspirating fluids from tubes, vessels or reagent containers. The system according to the invention uses a fluid delivery module to dispense fluid into the device according to the invention or/and remove liquid from the device. For example, applying a fluid to the device can be made by either applying the fluid under pressure to the device to press the fluid into the device or by applying negative pressure to the cavity so as to suck fluid into the device and removing or delivering fluid from the device to the outside can be achieved by either applying pressure to the cavity, e.g. by pumping a fluid, such as a liquid or a gas through a first fluid port, or applying negative pressure to the cavity so as to suck the fluid through a fluid port.

In a very preferred use, the instrument further contains supplemental means to perform an analysis, e.g. a heating element. This heating element is positioned such that it can contact the device at a position, wherein the heat can be used to heat up fluid within the device, preferably when the fluid is contained in a cavity within the device. An example of an instrument comprising a heating element is a thermocycler. Thermocyclers are generally known to apply a profile of different temperatures in repeated manner to a fluid. An exemplary thermocycler is described in EP 236 069. Preferred heating elements are Peltier elements or resistance heating elements.

In order to perform detection of properties or change of properties of the liquid during processes performed in the device, the instrument further can comprise a detection module. Appropriate detection modules are generally known and depend upon the kind of property or property change performed during the presence of the liquid in the device. For example, if the property is a change in an optical signal, for example a fluorescent signal, the detection module will comprise a light source positioned in the instrument such that the device, preferably a chamber in that device, can be irradiated, and an irradiation receiving unit, preferably a light sensitive cell for receiving irradiation from the liquid contained in the device and transmitting an electrical signal to an evaluation unit.

If the process to be performed in the device requires connectivity of components of the device, such as electrodes or heating foils in the device to an electric circuit of the instrument, such connectors are preferably provided on the instruments on positions that are located such that the connectors on the instrument are connected to their counterparts on the device, when the device is inserted into the instrument.

Preferably, the system according to the invention comprises in addition a fluid container (e.g. for waste collection) or/and one or more reagent containers.

A further subject of the invention is the use of a device according to the invention in a method for the isolation of components of a fluid from said fluid.

Another subject of the invention is the use of the device according to the invention for the analysis of a sample e.g. in an in-vitro diagnostic test.

For such uses, the fluid, preferably a sample to be analyzed or/and reagents, is preferably introduced into the device into a channel leading to a chamber. The fluid is forced to pass the channel until it reaches the inlet port of the chamber. There the fluid enters the chamber. In case that the matrix completely fills the chamber, the fluid then enters the matrix. Depending upon the dimensions of the inlet port, the matrix will be entered at a limited or broader contact front and may be distributed to evenly enter flow paths through the matrix. Due to the flow resistance profile in the matrix, e.g. created by different Degrees of Compression on the different paths, the fluid will flow through the matrix substantially uniform, such that similar conditions for binding components from the fluid to the matrix are created. For example, in prior art methods without unequal compression most of the fluid had flown through the flow path directly connecting the inlet port with the outlet port. This had the consequence that on this path, the binding capacity of the matrix is quickly exhausted, so that no more components can be bound, and even components not been bound will escape the matrix through the outlet port into the channel, and may be discarded as waste or may be guided to chambers where they may disturb the performance of further treatment steps.

If desired, the components bound to the matrix can be washed to further purify them from contaminating substances or/and can be eluted from the matrix into a fluid to be removed from the matrix or/and the chamber or/and the device. The resulting fluid can be subjected to further treatment of the purified or modified components inside or outside of the device.

Therefore, if components are to be eluted from the matrix by the fluid, they will leave the chamber earlier from the shorter flow paths and may be eluted from matrix on longer paths much later or even may stay on the matrix. This is connected to a reduced elution yield and undesirable. In the present invention this undesired effect can be reduced.

In a particularly preferred embodiment, the eluted fluid is transferred through a channel beginning at the outlet port of the first chamber containing the matrix to another chamber where the components comprised in the fluid are subjected to further treatment, e.g. amplification of nucleic acids, and even further steps, like detection of the nucleic acids amplified. If desired, reagents can be added to the fluid to assist in the analysis. A wide variety of methods for further treatment are known in the art.

For example, detection can start in the second chamber by irradiating the fluid in the second chamber with light of a wave length at which one of the components or reagents in the fluid has a measurable absorption. Determination of light leaving the chamber, for example by fluorescence, can be used to determine the absorbance of the fluid or any changes in absorbance of the fluid over time or compared to a standard fluid.

In a very preferred embodiment of this method of analysis, the component of the fluid to be analyzed is a nucleic acid suspected to be contained in the fluid, for example, parts of the genome of hepatitis C virus. The reagents for analysis will then contain primers for the amplification of a particular fragment of said nucleic acid and a probe for binding to the amplified fragment. A very preferred embodiment of such reaction is disclosed in EP 543 942. In order to apply thermo cycles to the liquid contained in the chamber, the instrument used contains a combined heating/cooling block to bring the content of the chamber to the temperature in a profile as needed to amplify the nucleic acids.

An advantage of the device according to the present invention is that the treatment of a fluid in the chamber is more reliable and complete, e.g. binding and elution of components of the fluid or of the matrix is more complete and uniform. Particularly, smaller amounts of reagents for treatment of bound components, like washing solution, are needed for successful treatment, e.g. purification, of components of fluids bound to the matrix. Elution into a small amount of elution buffer is possible. In another view, the invention allows reduction of shortcuts relevant for the treatment, which results in the above advantages. This device allows better systems, methods and uses comprising such devices.

While the foregoing invention has been described in some detail for purposes of clarity and understanding, it will be clear to the one skilled in the art from a reading of this disclosure that various changes in form and detail can be made without departing form the true scope of the invention. For example, all the techniques and apparatus described above can be used in various combinations. All publications, patents, patent applications, and/or other documents cited in the application are incorporated by reference in their entirety for all purposes to the same extent as if each individual publication, patent application, and/or other document were individually indicated to be incorporated by reference for all purposes

REFERENCE NUMERALS 1 device
2 fluid introduction port
3 fluid removal port
4 channel
5 channel
6 inlet port
7 outlet port
8 chamber
9 side wall
10 shorter length flow path
11 longer length flow path
12 matrix
13 protrusion
14 sealing wall
15 body
16 punching tool
17 fleece
18 plunger
19 funnel
20 groove
21 punched matrix

EXAMPLES

Example 1

Figure 6:
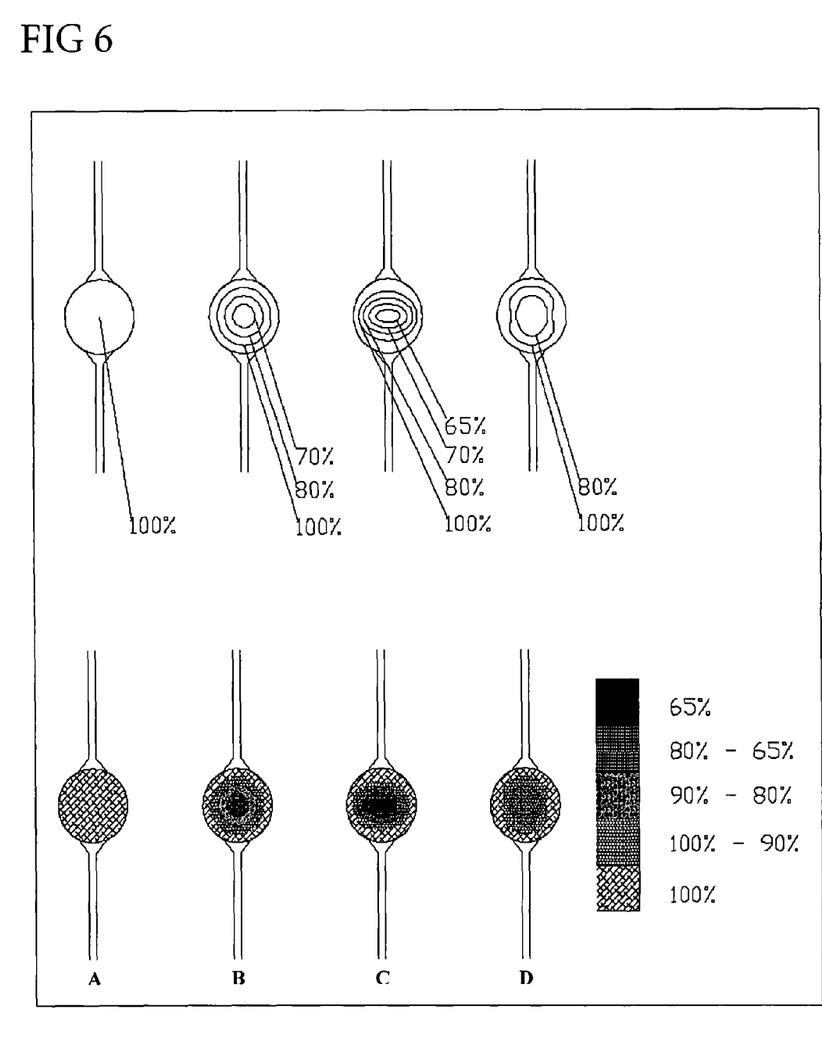
In FIG. 6 there is shown Degree of Compression in a prior art chamber (left hand side "A") and in several chambers according to the invention according to the invention ("B", "C", "D"). Upper row indicated as level curves, lower row indicating the same device as above but unequal DC indicated by various hatchings.

Preparation of a Device for Determining the Flow Resistance as a Function of Height of a Chamber Fluidic devices for the isolation of nucleic acids for Molecular Diagnostics purpose were prepared as follows:

A body having a cuboid form of 2 mm×20 mm×40 mm has at one of the flat side a circular groove of a diameter of 4.8 mm and a varying depth between 1 and 0.64 mm. Typical designs are shown in FIG. 6. The variably implemented flow-resistances were from 100% to 160%. The flow-resistance was tuned by the height of the chamber. According to the property of the inserted matrix (FIG. 2) 100% flow resistance=1 mm height, and 160% flow resistance=0.64 mm height, (intermediate flow-resistances interpolated).

Channels having a depth of 400 μm and a breadth of 400 μm reach from each long side to the groove, thus forming an inlet port and an outlet port. The form of the channels and the chamber is shown schematically in FIG. 1.

The fluidic devices were prepared from polypropylene by injection molding.

A fleece of glass fiber (200 g/m$^2$), thickness uncompressed 1.8 to 2.2 mm with a diameter of 5.0 mm punched out of a fleece was introduced into the groove (see FIG. 7).

A thermo seal laminate foil (30 micron PP on 110 micron aluminum, commercially available from Alcan, Switzerland) was hot-sealed on the full side of the body containing the groove, thus covering and compressing the fleece into the chamber.

Example 2

Determination of the Flow Resistance as a Function of the Height of the Chamber

The flow resistance was measured by measuring the flow-rate through at constant differential constant in the devices as prepared in Example 1. The results are given in FIG. 2. The Y-axis shows the DC divided by 100, the X-axis shows the flow resistance in %. A DC of 1.00 (100%) corresponds to a flow resistance of 100%.

Example 3

Device According to the Invention and Determination of the Flow Homogeneity

Figure 3:
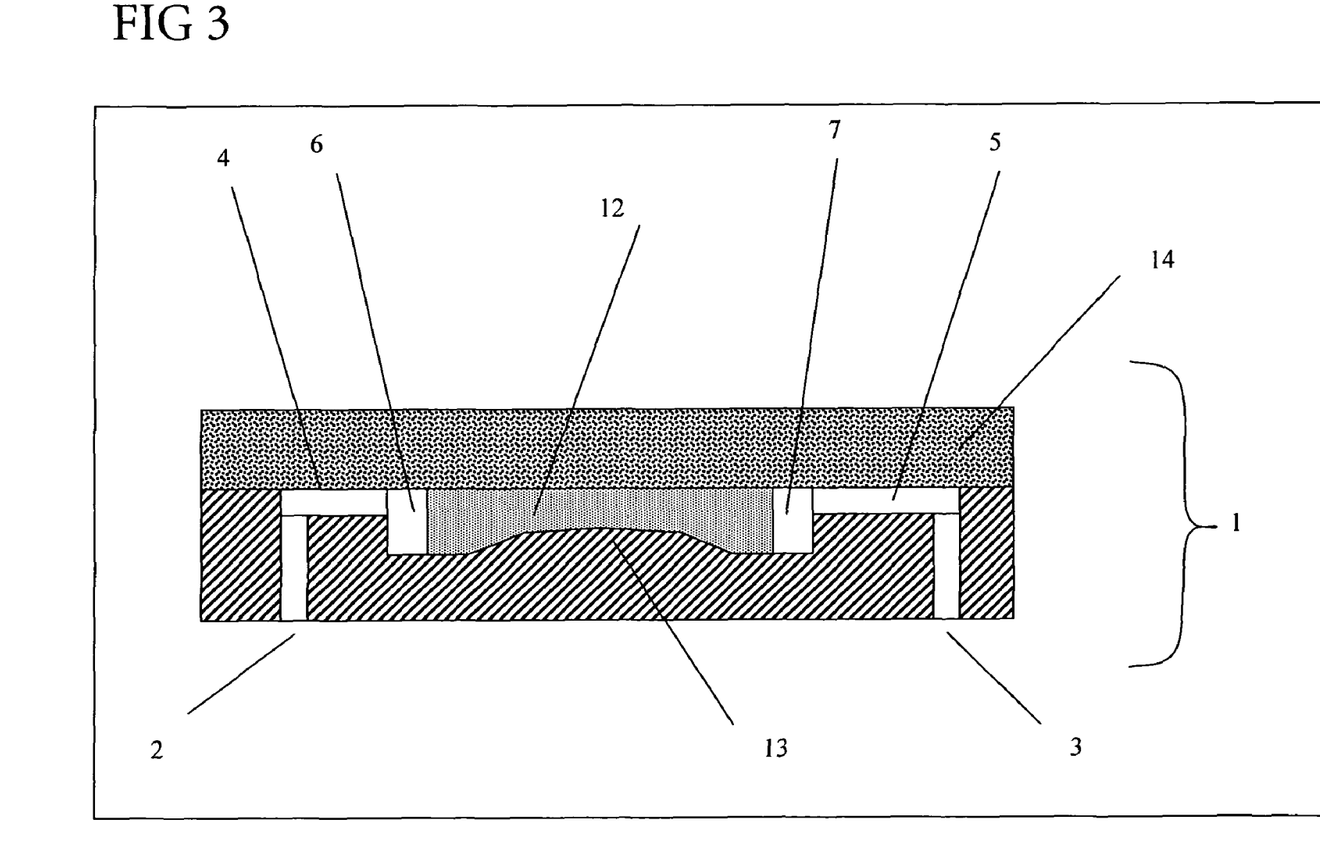
In FIG. 3 there is shown a cut through a device according to the invention cut through the inlet and outlet port, along the shortest length flow path.

A device is prepared as in Example 1, but the groove (20) had a protrusion (13) of a maximum of 0.7 mm in the center of the groove as shown in cut view in FIG. 3.

Figure 4:
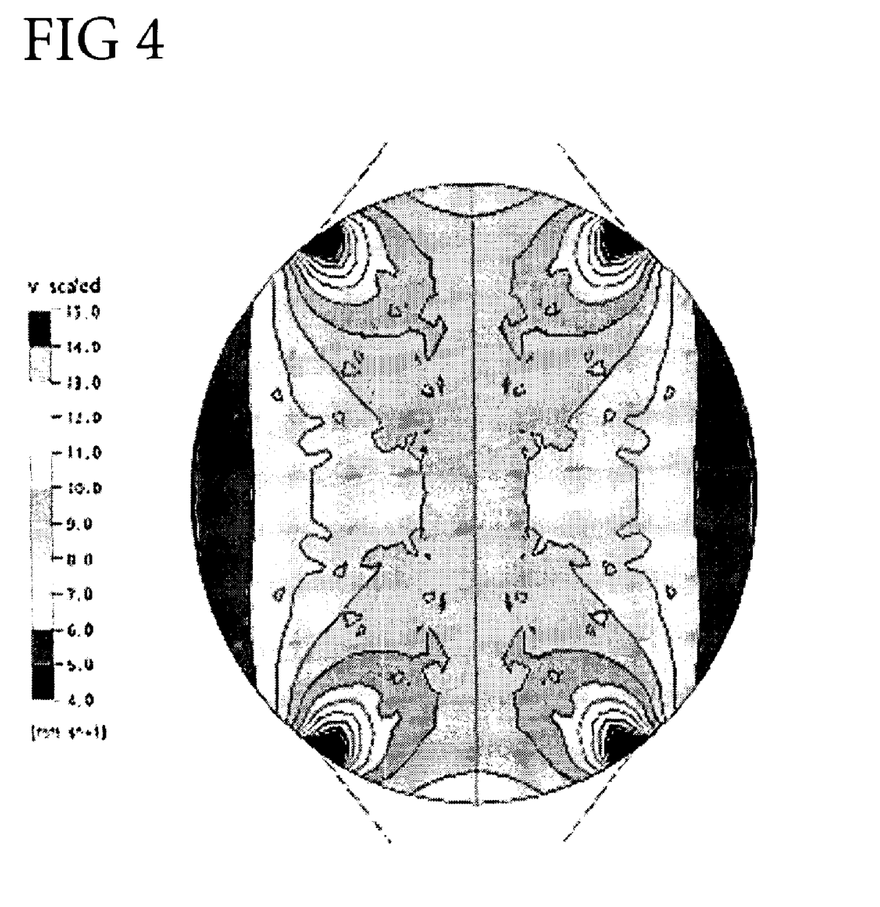
In FIG. 4 there is shown the flow homogeneity in a prior art chamber (using equal compression), as in FIG. 6 "A". The flow-rate at each point is displayed as a grey-scale color.

The flow homogeneity within a device according to the prior art (no compression) is shown in FIG. 4. It can be seen that the majority of the flow lies between 6 and 10 mm/sec.

Figure 5:
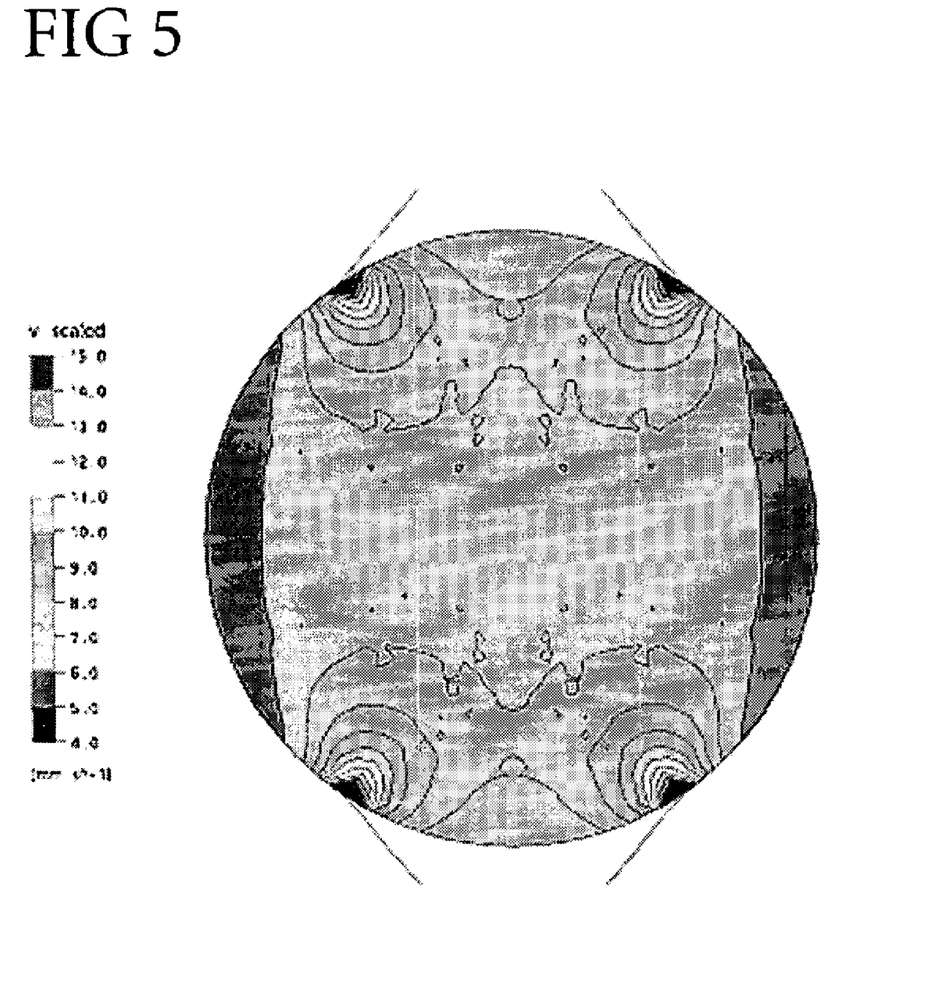
In FIG. 5 there is shown the flow homogeneity in a chamber according to the invention, as in FIG. 6 "B". The flow-rate at each point is displayed as a grey-scale color.

The flow homogeneity within a device according to the invention is shown in FIG. 5. It is evident that the same area as in the prior art is now having a flow between 6 and 8 mm/sec, i.e. the homogeneity is much higher, that means the area of similar flow within the matrix is distributed over a larger area than in the prior art device.

Based on the above, models for modifications of the compression were made (compression defined in the upper row) and the resulting flow homogeneities/flow resistances (lower row) were calculated. The result is shown in FIG. 6. The left hand side model is the prior art model with no compression (DC is 100%, SDC is 0%).

The invention claimed is:

1. A fluidic device containing a flow through chamber, said chamber comprising:
an upper wall and an opposing lower wall separated by a distance,
one or more protrusions configured on at least one of said upper wall and said lower wall, the one or more protrusions successively reducing the distance between said upper wall and said lower wall, an inlet port, an outlet port, both ports are designed to allow a fluid to be treated in said chamber by flowing through said chamber, a fluid permeable, compressible matrix located in the chamber between said upper wall and said lower wall, and between said inlet port and said outlet port, said compressible matrix having a higher flow resistance at a lower value of the Degree of Compression compared to at a higher value of the Degree of Compression a plurality of flow paths leading from said inlet port to said outlet port through said matrix comprising shorter length flow paths and longer length flow paths, characterized in that said matrix is unequally compressed by said one or more protrusions, being more strongly compressed in the shorter length flow paths than in the longer length flow paths, such that the flow through times through said plurality of flow paths are at least partially equalized.

2. The device according to claim 1, wherein said dimension is orthogonal to the shorter length flow path.

3. The device according to claim 1, wherein the average degree of compression is smaller than 100% and the span of degree of compression is at least 5%.

4. The device according to claim 1, wherein the average degree of compression is smaller than 90% and the span of degree of compression is at least 10%.

5. The device according to claim 1, wherein the matrix is a fiber based fleece or a porous body.

6. The device according to claim 1, wherein the difference in compression is realized by a different height of the chamber.

7. The device according to claim 1, wherein the difference in compression is created by a different height of the chamber.

8. The device according to claim 1, wherein the height of said chamber, between said upper wall and said lower wall, is between 100% and 20% of the largest height of said chamber.

9. The device according to claim 1 wherein the ratio of the maximum distance between the side walls of the chamber and the maximum distance between the upper wall and the lower wall of the chamber is between 2:1 and 500:1.

10. The device according to claim 1, wherein the ratio of the length of the matrix measured along said shorter flow path to the width of said matrix is between 20:1 and 1:20.

11. The device according to claim 1, wherein the minimum distance between the upper wall and the lower wall is equal to or greater than 0.2 and equal to or less than 3 mm.

12. The device according to claim 1, wherein the geometry of said chamber between said inlet and said outlet is plane symmetric regarding the connection between said inlet and said outlet port.

13. The device according to claim 1, wherein the shape of the chamber harboring the matrix is circular or rectangular with rounded corners.

14. The device according to claim 1, wherein the shape of the matrix for the circular chamber is cylindrical.

15. The device according to claim 1, wherein the matrix comprises a material capable of binding a component of the fluid.

16. The device according to claim 1 wherein the matrix is compressed in said chamber in two orthogonal dimensions orthogonal to the flow direction, and wherein in at least one direction the degree of compression is varied.

17. The device according to claim 1, wherein said permeable, compressed matrix fills said chamber completely on at least one cross-section orthogonal to the flow paths of the chamber between said inlet port and said outlet port.

18. The device according to claim 1, wherein the matrix is a solid phase absorber, an ion exchanger or a carrier of reagents or a filter.

19. The device according to claim 1, characterized in that said matrix is a fleece.

20. The device according to claim 1, wherein said inlet and outlet ports are located at opposing positions of the chamber.

* * * * *